United States Patent
Weiss et al.

(10) Patent No.: US 8,275,459 B2
(45) Date of Patent: Sep. 25, 2012

(54) WIRELESS FEEDTHROUGH FOR MEDICAL IMPLANTS

(75) Inventors: Ingo Weiss, Berlin (DE); Stefan Knorr, Berlin (DE)

(73) Assignee: Biotronik CRM Patent AG (CH)

( * ) Notice: Subject to any disclaimer, the term of this patent is extended or adjusted under 35 U.S.C. 154(b) by 651 days.

(21) Appl. No.: 12/469,305

(22) Filed: May 20, 2009

(65) Prior Publication Data

US 2010/0298909 A1  Nov. 25, 2010

(30) Foreign Application Priority Data

May 23, 2008  (DE) .......................... 10 2008 024 857

(51) Int. Cl.
*A61N 1/372* (2006.01)

(52) U.S. Cl. ............... 607/36; 607/37; 607/57; 607/50; 607/32; 607/60

(58) Field of Classification Search ............ 607/36–37, 607/57, 50–51
See application file for complete search history.

(56) References Cited

U.S. PATENT DOCUMENTS

| | | | |
|---|---|---|---|
| 4,614,192 A | 9/1986 | Imran et al. | |
| 6,654,638 B1 * | 11/2003 | Sweeney | 607/9 |
| 6,802,811 B1 | 10/2004 | Slepian | |
| 7,489,967 B2 * | 2/2009 | Von Arx et al. | 607/32 |
| 7,580,750 B2 * | 8/2009 | Doron et al. | 607/36 |
| 7,684,872 B2 * | 3/2010 | Carney et al. | 607/116 |
| 7,912,548 B2 * | 3/2011 | Mi et al. | 607/36 |
| 7,949,396 B2 * | 5/2011 | Mi et al. | 607/36 |
| 2006/0009818 A1 * | 1/2006 | Von Arx et al. | 607/60 |
| 2006/0149329 A1 * | 7/2006 | Penner | 607/32 |
| 2006/0167500 A1 * | 7/2006 | Towe et al. | 607/3 |
| 2007/0016274 A1 * | 1/2007 | Boveja et al. | 607/101 |
| 2007/0270007 A1 | 11/2007 | Mueller et al. | |
| 2009/0093855 A1 | 4/2009 | Mueller et al. | |

FOREIGN PATENT DOCUMENTS

| | | |
|---|---|---|
| DE | 10 2004 014 288 A1 | 10/2005 |
| DE | 10 2006 003 224 A1 | 6/2007 |
| WO | WO 02/056761 A2 | 7/2002 |

\* cited by examiner

*Primary Examiner* — Niketa Patel
*Assistant Examiner* — Joseph Stoklosa
(74) *Attorney, Agent, or Firm* — Craig A. Fieschko, Esq.; DeWitt Ross & Stevens S.C.

(57) ABSTRACT

An implantable arrangement including an implantable electromedical device having an exterior wall and an implantable sensor and/or actuator outside of the exterior wall. The sensor and/or actuator are in signal connection with the implantable device via an electric stage and a mechanical stage arranged in series, wherein the mechanical stage sends and/or receives mechanical vibration signals through the closed exterior wall, and the electrical stage sends and/or receives the same signals in electrical form.

20 Claims, 6 Drawing Sheets

Frequency 1:

Frequency 2:

WIRELESS FEEDTHROUGH FOR MEDICAL IMPLANTS

FIELD OF THE INVENTION

The invention relates to an implantable device, in particular an electromedical device in signal connection with an implantable sensor and/or actuator.

BACKGROUND OF THE INVENTION

In recent years, medicine has advanced to the extent that more and more highly developed implantable devices have been developed for treating a wide variety of physical conditions, and to support various body functions. Many of these therapeutic devices are operated with electric power and/or introduce this power directly into body tissue for treatment and/or support of body functions.

To make these devices interactive, implantable sensors and/or actuators that are in constant connection with the device are used, as known from U.S. Pat. No. 6,802,811 B1, for example. The sensors can monitor heart activity or blood flow, for example, while the actuators stimulate certain nerves or organs in the body.

Many implants are remotely operable, i.e., they can be externally activated, controlled, and/or queried regarding their influence on the body, and can remotely supply information about the patient's condition. There are a number of established systems, as well as extensive literature, for implementation of this remote effect (telemetry).

WO 02/056761 discloses a system wherein information about the condition of the implantable device, as well as information about the measured values detected by a sensor connected to the device, is transmitted by ultrasound to an external monitoring unit. The acoustic energy may also be used to store energy in the implantable device. Such a system allows continuous monitoring of the patient, while at the same time avoiding additional surgical procedures to replace the battery on the device, for example. The sensors and/or actuators are interactive elements at the site of the implant, but they are not remotely operable and instead are connected to the implantable device by electric lines.

An implantable device usually includes a housing, which holds the electronic controls, capacitors and batteries. To connect the electric lines from the sensors and/or actuators to the device, a wire or another conductive structure passes through the housing for each pole. With the usually metallic implant housings, each wire passing through the housing must be insulated. However, there is always a galvanic connection between the inside and the environment of the implant.

DE 10 2006 003 224 A1 discloses an implantable device including a connection body that is attached to the housing and has at least one electric connection, but usually two to four electric connections, arranged in one or more externally accessible cavities of the connection body, with the connections being used to connect one or more electrode lines.

Such feedthroughs are critical components with respect to the imperviousness and mechanical stability of the implants. The reason for this is the mechanical connection between the metal housing and the feedthrough which is often made of ceramic. Furthermore, the manufacturing complexity is great and assembly of the feedthroughs is very complex. A galvanic connection through the housing wall also increases the susceptibility of the implant to electromagnetic alternating fields, in particular when a long electrically conducting structure is connected outside of the implant.

SUMMARY OF THE INVENTION

An object of the invention is to provide an improved implantable arrangement with a lower manufacturing complexity, such that signal transmission between the components inside the housing and outside the housing takes place with a high immunity to interference and in a manner that does not impair the imperviousness of the housing even during prolonged use.

This object is achieved by an implantable arrangement having the features set forth in the accompanying claims.

The invention includes the important consideration of implementing the signal transmission between the components arranged inside and outside of the housing without needing a line connection through the housing. The invention involves an implantable arrangement including an implantable device with an exterior wall, and an implantable sensor and/or actuator in communication with the implantable device, with the implantable sensor and/or actuator being situated outside of the exterior wall in the use state. The signal connection between the sensor and/or actuator and the device has an electric stage, plus a mechanical stage connected in series with the electric stage between the device and the sensor and/or actuator. This mechanical stage is formed by signal transmission by means of mechanical vibrations through the closed exterior wall.

It follows from this that the signal transmission takes place in a potential-free manner. Furthermore, the transmission occurs in a certain frequency range, while different polarities can be transmitted through the exterior wall with frequency coding. In the case of metallic implants in particular, the electronics are more reliably protected from electromagnetic interference (EMI), in particular strong alternating fields, e.g., as in magnetic resonance imaging (MRI).

The exterior wall may be made of a conductive or insulating material, in particular a metal, plastic, ceramic or any material that may be considered for an implant. This yields a lower mechanical sensitivity, a higher imperviousness of the implantable device, and a lower manufacturing complexity.

A preferred version of the invention involves a transducer within the mechanical stage that is made of a piezoelectric material, and that converts the electric signals into mechanical vibrations or, conversely, converts mechanical vibrations into electric signals. Alternatively, the mechanical stage may also have a nonpiezoelectric converter. Examples include a magnetic coil arrangement that converts mechanical vibrations into a variation in current and/or voltage, or vice versa.

To transmit mechanical vibrations through the closed exterior wall, piezoelectric converters may be arranged on opposing sides of the exterior wall. In particular, at least one of the piezoelectric transducers is connected to the exterior wall in such a way that it induces vibrations directly in the exterior wall. In some systems, however, signal propagation may be accomplished by mechanical means on only one side of the exterior wall of the device, so the arrangement includes only one piezoelectric transducer (or some other electromechanical transducer).

As an alternative, in order to conduct the mechanical vibrations to a transducer situated at a distance from the exterior wall, at least one element that serves to conduct the mechanical vibrations may be provided in the mechanical stage. In this way, the conversion may take place at a location at a distance from the exterior wall, so there is no electric connection between this conversion location and the exterior wall. It is advantageous if the area between the conversion location and the exterior wall is insensitive to electromagnetic interference (EMI).

This conductive element may be made of a dielectric material or any suitable material that can form an effective mechanical waveguide.

The piezoelectric transducer has contact faces on which are arranged electric lines for feeding and/or conducting electric signals.

The geometry and location of the contact faces of the transducer are important parameters which, together with the piezoelectric material, have a great influence on the resonant frequency.

To increase the deformation amplitude of the transducer and therefore the signal amplitude of its output signal, it may be made of a stacked structure in which piezoelectric layers and electrode lines are alternately stacked one above the other.

The transducer, which is used to generate the mechanical vibrations, is expediently controlled with a resonant circuit, with the piezoelectric transducer functioning as a capacitor which jointly determines the inherent electric frequency of the resonant circuit. To generate multiple frequencies and/or discrete frequencies, the resonant circuit may be tuned. This is accomplished by connectable capacitors, for example.

In another version of the invention, multiple piezoelectric transducers are arranged side-by-side outside of the exterior wall. These transducers have different resonant frequencies, so that the piezoelectric transducer inside the exterior wall is controlled with an alternating voltage of the resonant frequency of one or more transducers on the outside. This makes it possible to implement the same function as with an arrangement in which only a single piezoelectric element is provided outside of the exterior wall, and multiple piezoelectric transducers are arranged side-by-side inside the exterior wall.

There is also the possibility of forming transducer pairs that are in resonance with one another along the interior and exterior walls, such that multiple piezoelectric transducers having different resonant frequencies are arranged side-by-side both inside and outside the exterior wall.

The invention also involves the use of an element that serves to further propagate the mechanical vibrations, enabling the conversion into electric signals at a remote location at a distance from the exterior wall.

In another version, a piezoelectric transducer formed with an uneven thickness is provided on at least one side of the exterior wall. Such a transducer therefore has different natural frequencies occurring at different locations. Such a special transducer thus corresponds functionally to a parallel circuit of multiple transducers having different resonant frequencies, as mentioned above, but this can save space in comparison and may also be less expensive. To expand the frequency range, a piezoelectric transducer characterized by an uneven thickness may be provided both inside and outside of the exterior wall.

In a useful version of the invention, the mechanical vibrations are converted into electric signals and relayed over an electrode line to an electrode, which is designed in particular as a stimulation electrode and/or sensing electrode for stimulation of electrically stimulable tissue (myocardium, areas of the brain or the cochlear nerve, etc.) and/or for detecting tissue potentials. Likewise, however, the inventive type of signal transmission may also be used in arrangements that do not include any electrodes, e.g., optical sensors (with a downstream optoelectronic transducer) or mechanical actuators (with an upstream electromechanical transducer).

Input/output of the electric signals takes place over standardized connections, e.g., IS-1 or IS-4 and/or other future standardized plug connections, or an independent connector system.

To be able to rectify the electric signals and/or the alternating voltage, the electric stage may additionally have a rectifier.

To protect the mechanical stage of the signal transmission which is in the exterior wall and/or to design it to be more stable, a cover is preferably provided outside of the exterior wall. The electrode line is then optionally connected to this cover, such that the line ends protrude out of the cover and are in communication with the sensors and/or actuators.

In an especially useful version of the invention, the cover may have two connections, which are connected to the electrode line and the piezoelectric transducers outside of the exterior wall to provide additional possible connections for the sensors and/or actuators in addition to the electrode ends protruding out of the cover.

In another version of this invention, a replaceable electrode connection structure which is provided can be mounted directly outside on the exterior wall. The replaceable structure here has an electrode housing and an electrode line attached to the housing. The structure includes at least one piezoelectric transducer for converting the mechanical vibrations into electric signals, with the electrode line ends protruding out of the electrode housing. The mechanical attachment of this replaceable structure may be accomplished by different methods. For example, a type of bayonet closure, a screw connection and a clamp attachment are possible. The advantage of such an arrangement is the possibility of replacing only a portion of the implantable arrangement, if necessary, which yields cost savings.

The invention may be used in various areas, e.g., in the field of cardiology, otolaryngology or orthopedics. In cardiology, the implantable device may be a heart stimulator, the implantable sensor may be a means for measuring the heart contractions, and the implantable actuator may be a means for delivering heart stimulation pulses. In otolaryngology, the implantable device may be used as a hearing aid implant and the actuator as means for stimulating the cochlear nerve. Various possible uses are also conceivable in orthopedics. For example, the implantable device may be an orthopedic implant and the sensor may be means for measuring physical stimuli or some other variables of the tissue such as temperature or pressure.

BRIEF DESCRIPTION OF THE DRAWINGS

Advantages and benefits of the invention will be apparent from the following description of a few selected exemplary versions with reference to the figures, in which.

DETAILED DESCRIPTION OF PREFERRED VERSIONS OF THE INVENTION

Figure 1:
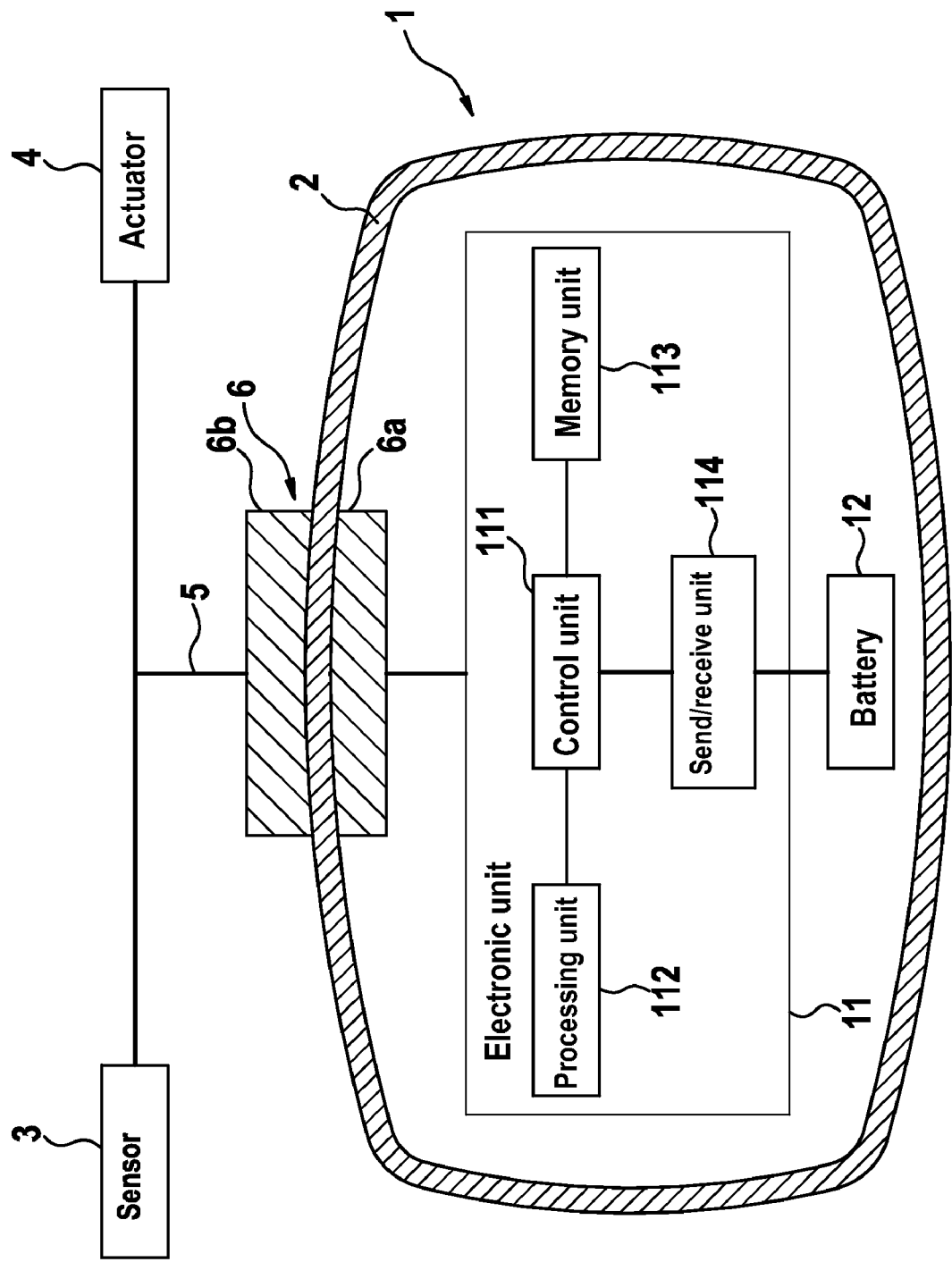
FIG. 1 shows a schematic diagram of an implantable arrangement according to the invention.

FIG. 1 shows an implantable device 1 having an exterior wall 2, which has a surface that is closed all the way around and is made of a single material, and two implantable electric components 3 and 4, which are arranged outside of the exterior wall 2 when in use. These components include a sensor (measurement sensor) 3 which might detect certain physical or chemical properties of a tissue or organ, and an actuator 4, which receives an input signal from the device 1 and thereby acts on a patient's body. The implantable sensor 3 and the implantable actuator 4 are in signal connection with the implantable device 1. The signals between the device 1 and the sensor 3 and/or actuator 4 are relayed by an electric stage 5 and a mechanical stage 6. The mechanical stage 6 is arranged in series with the electric stage 5 and has subsections 6a and 6b inside and outside of the exterior wall 2.

Inside the exterior wall 2, the device 1 has an electronic unit 11 which is in signal connection with the subsection 6a of the mechanical stage 6 inside of the exterior wall 2. The electronic unit 11 contains a control unit 111 for controlling the operation of one or more of the device 1, the sensor 3, and the actuator 4; a computer unit 112 and a memory unit 113 for computing and storing the measured values of the sensor 3 thereby detected; and a transmitting/receiving unit 114 for transmitting data by wireless communication to an external monitoring unit (not shown) and receiving control signals from such a unit. Furthermore, the implantable device 1 has a battery 12, which serves as a power source for supplying power to the electric elements of the electronic unit 11. The transmitting/receiving unit 114 may be used to periodically charge the battery 12 via a wireless power feed.

The mechanical stage 6 allows signal transmission through the closed exterior wall 2 by means of mechanical vibrations. In particular this stage 6 allows transmission of stimulation pulses generated by the implant electronics 11 to the actuator 4, and similarly transmission of signals from the sensor 3 to the electronic unit 11, without requiring a galvanic connection to pass through the exterior wall 2. It follows from this that the signal transmission is accomplished in a potential-free manner. Furthermore, the transmission takes place in a certain frequency range while different polarities can be transmitted through the exterior wall in a frequency-coded manner.

Figure 2:
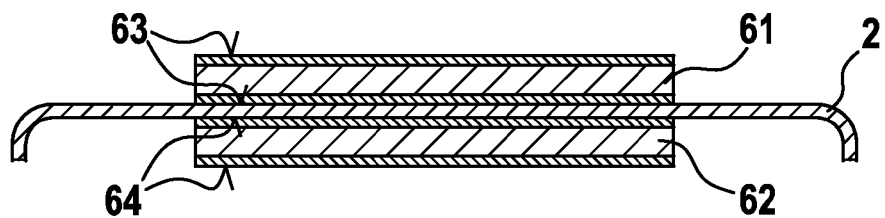
FIG. 2 shows a schematic diagram of the mechanical stage according to one version of the invention.

FIG. 2 shows a diagram of the mechanical stage 6, in which two transducers, in particular piezoelectric transducers 61 and 62, convert the electric signals into mechanical vibrations or, conversely, convert the mechanical vibrations into electric signals, each being arranged on one side or the other side of the exterior wall 2. The piezoelectric transducers 61 and 62 here are rigidly connected to the exterior wall in such a way that they can directly induce vibration of the exterior wall 2, and the other transducer (not controlled) can pick up the vibration directly.

Each transducer 61 and 62 has contact faces 63 and 64 to which electric lines are applied for further propagation of the electric signals. The electric signals are carried from the electronic unit 11 to the interior transducer 62, where they are converted into mechanical vibrations. The mechanical vibrations are transmitted via the exterior wall 2 to the external transducer 61, where they are converted into electric signals. Finally, these signals are relayed over electric lines to the actuator 4. In the opposite case, the electric signals are transmitted from sensor 3 to the electronic unit 11 inside the exterior wall 2.

Figure 3:
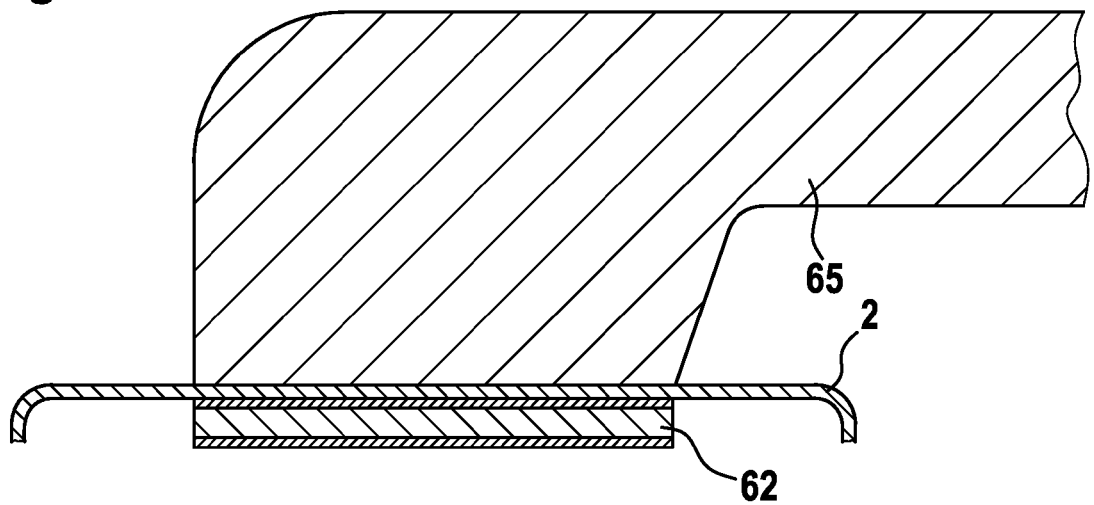
FIG. 3 shows a schematic diagram of the mechanical stage according to an alternative version of the invention.

FIG. 3 shows an alternative version in which a piezoelectric transducer is not provided directly on the exterior wall 2 on the outside but instead an element 65 (e.g., an essentially rod-shaped element) which serves to further conduct the mechanical vibrations is provided there. The conversion into electric signals may then take place at another location at a greater distance from the exterior wall 2. This element 65 may be made of dielectric material and/or any suitable material that yields an effective mechanical waveguide.

Figure 4A:
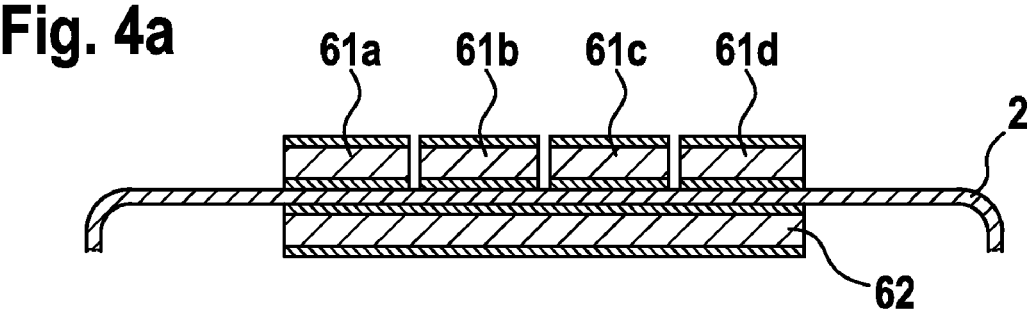
FIG. 4 shows schematic diagrams of the mechanical stage according to various other versions of the invention.

FIG. 4a shows an version of the mechanical stage 6 in which multiple piezoelectric transducers 61a, 61b, 61c and 61d are arranged side-by-side outside of the exterior wall 2. These transducers have different resonant frequencies and therefore allow frequency coding. The transducer 62 inside the exterior wall 2 is thus controlled with an alternating voltage according to the resonant frequency of one or more transducers 61a, 61b, 61c and 61d outside of the exterior wall 2. The transducer 62 is induced to mechanical vibration according to the frequency (frequencies) of the corresponding transducer(s) 61a, 61b, 61c and 61d, each of which generates the resonant mechanical vibration outside of the exterior wall 2.

Figure 4B:
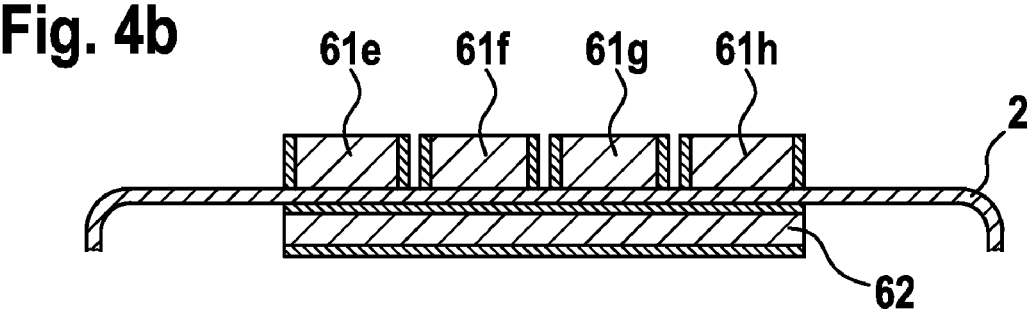

FIG. 4b shows a modified version in which the contact faces of the exterior transducers 61e, 61f, 61g and 61h are not arranged along the exterior wall 2 as in FIG. 4a but instead are arranged perpendicular to the exterior wall 2. A change in the contact face arrangement allows a change in the direction of vibration and thus allows a change in the resonant frequency of the transducers. The version shown in FIG. 4b facilitates the arrangement of electric lines on the contact faces in particular and improves the transmission of mechanical vibrations through the exterior wall 2.

Figure 4C:
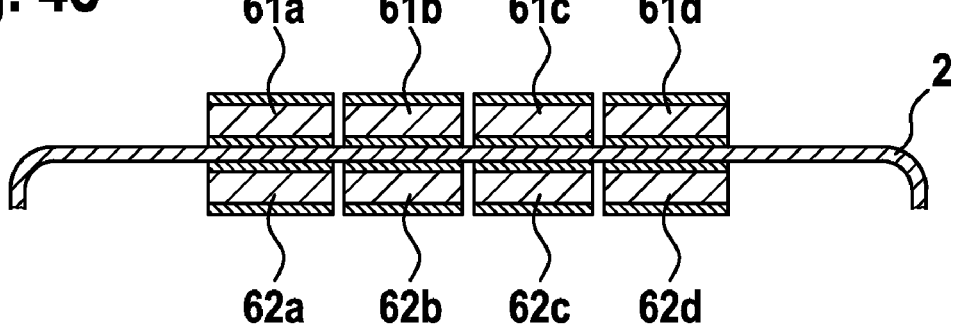

FIG. 4c shows another version of the mechanical stage 6 in which several piezoelectric transducers 61a, 61b, 61c, 61d and 62a, 62b, 62c, 62d are arranged side-by-side both inside and outside of the exterior wall 2. This increases efficiency because transducer pairs, e.g., 61a and 62a, are in resonance with one another. Furthermore, the individual transducers 62a, 62b, 62c and 62d are galvanically isolated inside of the exterior wall 2, so that they do not affect one another. They may even have the same frequency if the coupling of two different transducer pairs is not too strong.

Figure 5A:
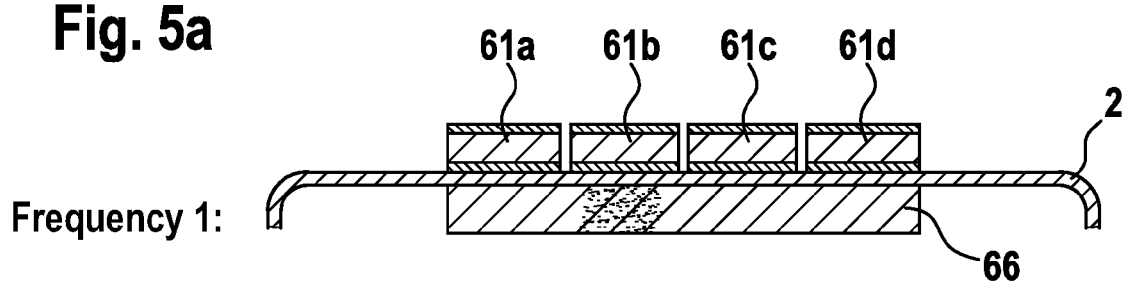
FIG. 5 shows a schematic diagram of the mechanical stage according to another version of the invention.
Figure 5B:
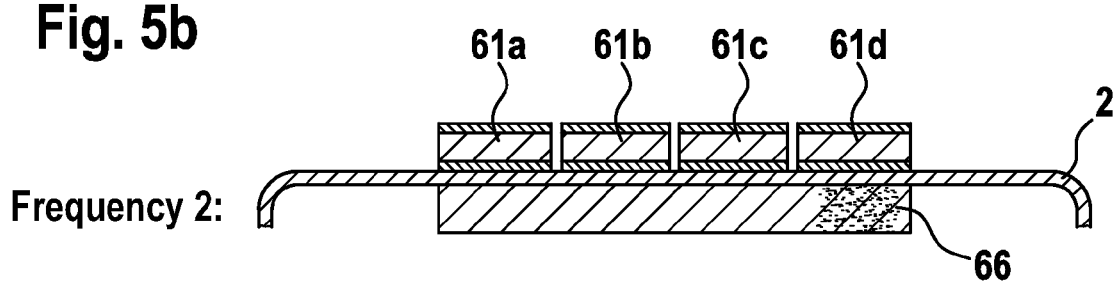

FIGS. 5a and 5b show an version of the mechanical stage 6 in which a piezoelectric transducer 66 with an uneven thickness is formed inside the exterior wall 2. Such a transducer has various natural frequencies, the mechanical vibrations of which strike different sites on the transducer. If the transducer 66 is energized with one of these natural frequencies, it vibrates especially strongly at the corresponding position. If a piezoelectric transducer having the same natural frequency is placed at the corresponding location on the other side of the exterior wall 2, then this transducer is energized primarily to vibrate. In FIG. 5a and FIG. 5b, this external transducer corresponds to the piezoelectric transducer 61b and/or 61d. The dark locations here indicate the frequency-dependent range where the vibration amplitude is at a maximum.

Figure 6A:
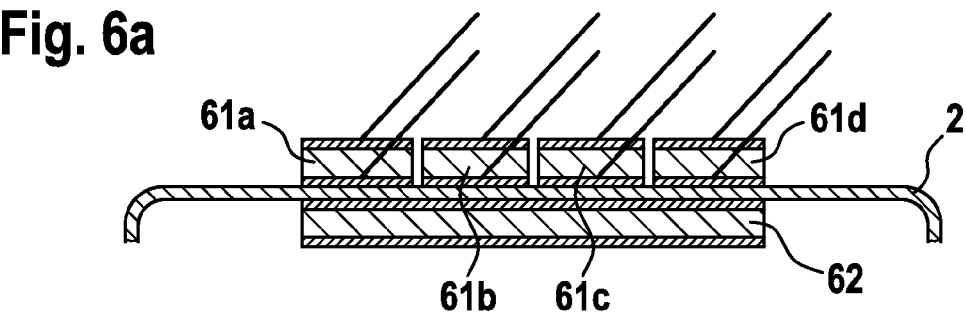
FIG. 6 shows schematic diagrams of the propagation of electric signals according to the various versions of the invention.

The electric signals may be conducted further in various ways. The simplest way is for each individual polarity to be transmitted individually by means of two electric lines, as illustrated in FIG. 6a.

Figure 6B:
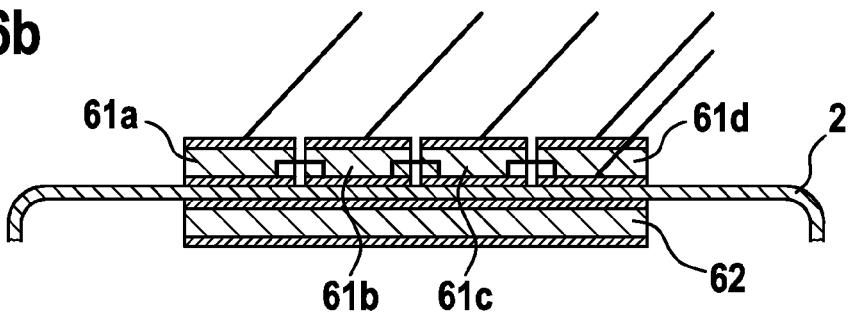
Figure 6C:
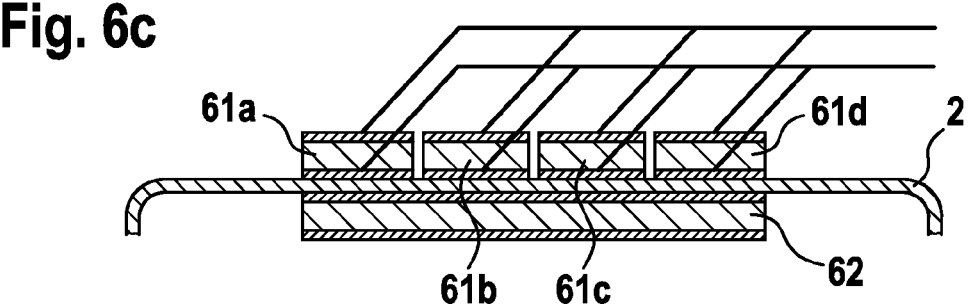
Figure 6D:
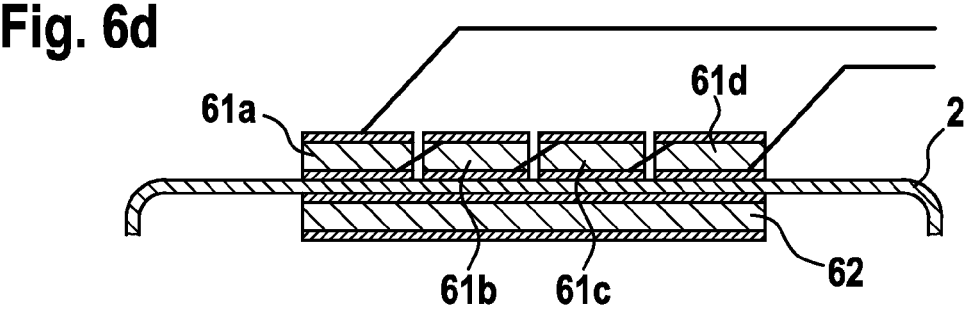
Figure 6E:
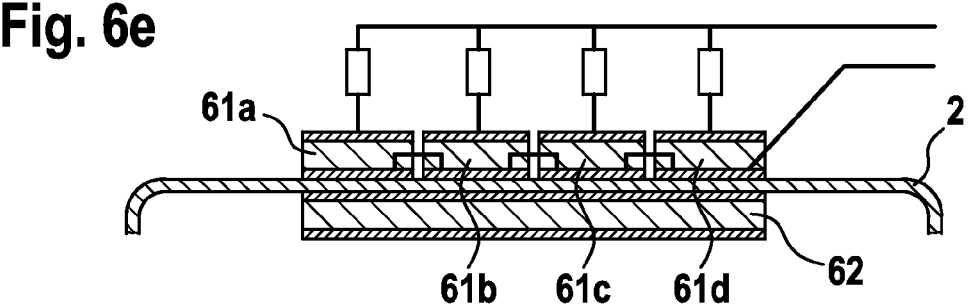

To reduce the number of electric lines, the reference potentials may be linked as shown in FIG. 6b. The number of lines can be further reduced if the various signals are transmitted at different frequencies. Different frequencies may be transmitted on the same line without having a mutual influence on one another. Possible circuits for combining the different alternating voltage signals may include a parallel circuit (FIG. 6c), a series circuit (FIG. 6d) or a mixture of the two circuits (FIG. 6e).

Figure 7:
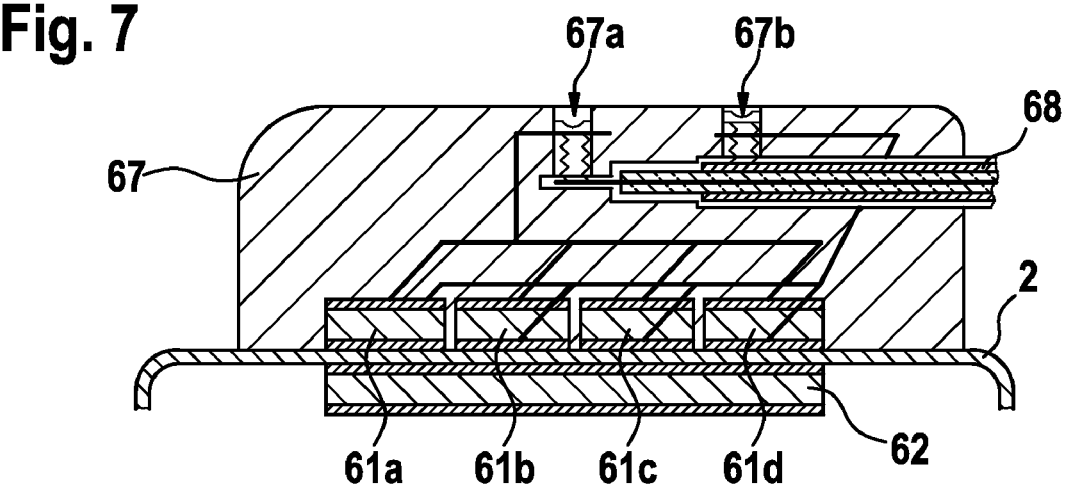
FIG. 7 shows a schematic diagram of the cover according to a special version of the invention.

FIG. 7 shows a design detail of the mechanical stage 6 in which a cover 67 is mounted outside of the exterior wall 2. The cover 67 covers the external transducers 61a, 61b, 61c and 61d to protect the mechanical stage 6, which is outside of the exterior wall 2, and to increase the stability of the arrangement. Within the cover 67, the electric lines arranged on the contact faces of the transducers 61a, 61b, 61c and 61d conduct the electric signals to an electrode 68 or apply signals coming from there to the transducers. The electrode line 68 is connected to the cover 67 in such a way that its ends protrude out of the cover 67 and are in signal connection with the sensor 3 and/or actuator 4 through the electric stage 5.

As an additional possible connection for the sensor 3 and/or actuator 4, the cover 67 has two connections 67a and 67b, which are connected to the electrode line 68 and the transducers 61a, 61b, 61c and 61d, which are outside of the exterior wall 2.

A signal cable is expediently connected by standardized connections, e.g., IS-1 or IS-4 and/or other plug connections that will be standardized in the future or an independent plug system.

Figure 8:
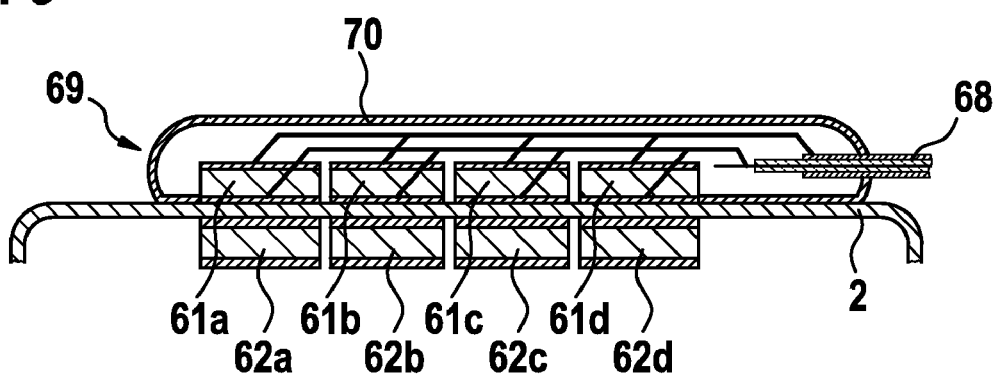
FIG. 8 shows a schematic diagram of the electrode housing of a replaceable electrode structure according to a preferred version of the invention.

FIG. 8 shows a replaceable electrode connection structure 69 which can be mounted directly on the exterior wall 2. This structure 69 has an electrode housing 70 on which the piezoelectric transducers 61a, 61b, 61c and 61d are mounted. The transducers are in contact with the exterior wall 2 through which they can transmit the mechanical vibrations to the respective transducers 62a, 62b, 62c and 62d situated inside the exterior wall 2. The transducers 61a, 61b, 61c and 61d are each connected to an electrode line 68 which is also attached to the electrode housing 70. Furthermore, the ends of the electrode line 68 protrude out of the electrode housing 70 and are in signal connection with the sensor 3 and/or the actuator 4.

Figure 9:
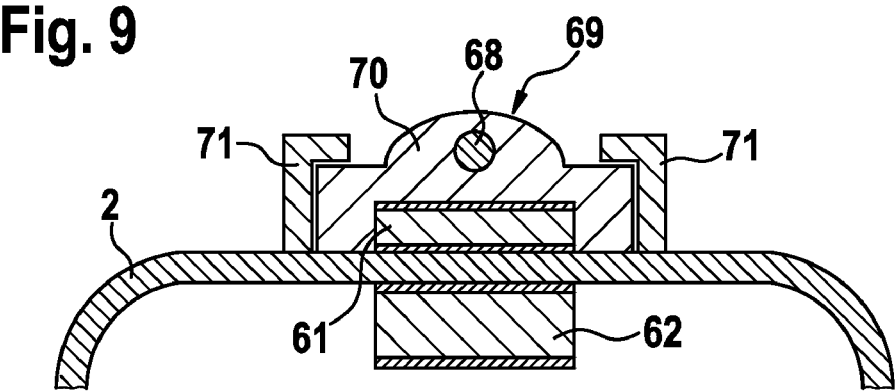
FIG. 9 shows a schematic diagram of the attachment of an electrode connecting structure according to a preferred version of the invention.

The mechanical attachment of this replaceable electrode connection structure 69 may be accomplished in various ways. FIG. 9 illustrates an electrode connection structure 69 which is snapped or inserted into rails 71 attached to the exterior wall 2 of the implant.

Otherwise, the invention is not limited to the examples and features described above but instead is limited only by the scope of protection of the following claims.

What is claimed is:

1. An implantable electromedical arrangement including:
   a. an implantable first device having an exterior wall, and
   b. an implantable second device including a sensor and/or an actuator:
      (1) situated outside of, and spaced from, the exterior wall of the first device, and
      (2) being in communication with the first device via:
         (a) a mechanical stage sending and/or receiving mechanical vibration through the exterior wall of the first device, the mechanical stage having a first transducer and a second transducer on opposing sides of the exterior wall of the first device, and
         (b) an electrical stage conveying electrical signals between the mechanical stage and the sensor and/or the actuator, the electrical signals being converted from and/or to the mechanical vibration within the mechanical stage.

2. The arrangement of claim 1 wherein the first transducer of the mechanical stage includes at least one piezoelectric transducer converting between electric signals and mechanical vibrations.

3. The arrangement of claim 2 wherein the second transducer of the mechanical stage includes at least one piezoelectric transducer.

4. The arrangement of claim 2 wherein at least one piezoelectric transducer of the mechanical stage:
   a. defines a portion of a resonant circuit, and
   b. defines a capacitance which at least partially defines the electric natural frequency of the resonant circuit.

5. The arrangement of claim 2 wherein at least one piezoelectric transducer is formed with varying thickness.

6. The arrangement of claim 1 wherein the mechanical stage includes a first group of piezoelectric transducers on the exterior wall of the first device, the transducers of the first group having different resonant frequencies.

7. An implantable electromedical arrangement including:
   a. an implantable first device having an exterior wall, and
   b. an implantable second device including a sensor and/or an actuator:
      (1) situated outside of, and spaced from, the exterior wall of the first device, and
      (2) being in communication with the first device via:
         (a) a mechanical stage sending and/or receiving mechanical vibration through the exterior wall of the first device, the mechanical stage including:
            (i) a first group of piezoelectric transducers on the exterior wall of the first device, these transducers having different resonant frequencies; and
            (ii) a second piezoelectric transducer on the opposite side of the exterior wall from the first group of piezoelectric transducers, wherein the second piezoelectric transducer is tunable to the resonant frequency of two or more of the transducers within the first group of piezoelectric transducers, and
         (b) an electrical stage conveying electrical signals between the mechanical stage and the sensor and/or the actuator, the electrical signals being converted from and/or to the mechanical vibration within the mechanical stage.

8. An implantable electromedical arrangement including:
   a. an implantable first device having an exterior wall, and
   b. an implantable second device including a sensor and/or an actuator:
      (1) situated outside of, and spaced from, the exterior wall of the first device, and
      (2) being in communication with the first device via:
         (a) a mechanical stage sending and/or receiving mechanical vibration through the exterior wall of the first device, the mechanical stage including:
            (i) a first group of piezoelectric transducers on the exterior wall of the first device, these transducers having different resonant frequencies; and
            (ii) a second group of piezoelectric transducers on the exterior wall of the first device, these transducers:
               1) being on the opposite side of the exterior wall from the first group of piezoelectric transducers, and
               2) each having a resonant frequency which is at least substantially similar to a resonant frequency of a corresponding one of the piezoelectric transducers from the first group of piezoelectric transducers, and (b) an electrical stage conveying electrical signals between the mechanical stage and the sensor and/or the actuator, the electrical signals being converted from and/or to the mechanical vibration within the mechanical stage.

9. An implantable electromedical arrangement including:
a. an implantable first device having an exterior wall, and
b. an implantable second device including a sensor and/or an actuator:
(1) situated outside of, and spaced from, the exterior wall of the first device, and
(2) being in communication with the first device via:
(a) a mechanical stage sending and/or receiving mechanical vibration through the exterior wall of the first device, the mechanical stage including:
(i) a first group of piezoelectric transducers on the exterior wall of the first device, these transducers having different resonant frequencies; and
(ii) one or more second piezoelectric transducers on the opposite side of the exterior wall from the first group of piezoelectric transducers, wherein the second piezoelectric transducers are each at least substantially directly opposite one or more of the piezoelectric transducers in the first group of piezoelectric transducers, and
(b) an electrical stage conveying electrical signals between the mechanical stage and the sensor and/or the actuator, the electrical signals being converted from and/or to the mechanical vibration within the mechanical stage.

10. The arrangement of claim 1 wherein the first device lacks any conductors bearing electricity through the exterior wall of the first device.

11. The arrangement of claim 1 wherein:
a. the mechanical stage is enclosed in a cover which at least partly surrounds the mechanical stage, and
b. the cover is mounted on the exterior wall of the implantable first device.

12. The arrangement of claim 11 wherein:
a. at least a portion of the electrical stage is also enclosed within the cover,
b. the cover includes an aperture therein into which an electrode line is received, the electrode line being in electrical communication with the electrical stage.

13. The arrangement of claim 1 further including an element spacing the mechanical stage of the second device from the exterior wall of the first device, wherein the element conducts mechanical vibration therebetween.

14. The arrangement of claim 1 wherein:
a. the implantable first device includes a heart stimulator,
b. the implantable second device includes both:
(1) a sensor configured to measure contractions of the heart, and
(2) an actuator configured to deliver heart stimulation pulses.

15. An implantable electromedical arrangement including:
a. an implantable first device having an exterior wall, the implantable first device including a cochlear implant, and
b. an implantable second device including an actuator configured to deliver cochlear nerve stimulation signals, the actuator:
(1) situated outside of, and spaced from, the exterior wall of the first device, and
(2) being in communication with the first device via:
(a) a mechanical stage sending and/or receiving mechanical vibration through the exterior wall of the first device, and
(b) an electrical stage conveying electrical signals between the mechanical stage and the sensor and/or the actuator, the electrical signals being converted from and/or to the mechanical vibration within the mechanical stage.

16. An implantable electromedical arrangement:
a. the arrangement including:
(1) an implantable first device having an exterior wall, and
(2) an implantable second device including a sensor and/or an actuator:
(a) situated outside of, and spaced from, the exterior wall of the first device, and
(b) being in communication with the first device via:
(i) a mechanical stage sending and/or receiving mechanical vibration through the exterior wall of the first device, and
(ii) an electrical stage conveying electrical signals between the mechanical stage and the sensor and/or the actuator, the electrical signals being converted from and/or to the mechanical vibration within the mechanical stage;
b. wherein:
(1) the implantable first device includes an orthopedic implant, and
(2) the implantable second device includes a sensor configured to measure at least one of:
(a) temperature,
(b) force, and
(c) electrical signals.

17. An implantable electromedical arrangement including:
a. an implantable first device having an exterior wall,
b. an implantable second device including one or more of:
(1) a sensor, and
(2) an actuator,
situated outside of the exterior wall of the first device,
c. a vibrating element on one side of the exterior wall, the vibrating element emitting vibrations encoding signals:
(1) for delivery to, or
(2) received from,
the implantable second device;
d. a vibration transducer on the opposite side of the exterior wall, the vibration transducer receiving the encoded vibrations through the exterior wall and converting them to electrical signals.

18. The implantable electromedical arrangement of claim 17 wherein:
a. the vibrating element is within the exterior wall of the first device;
b. the second device includes an actuator receiving the electrical signals from the vibration transducer.

19. The implantable electromedical arrangement of claim 17 wherein:
a. the vibrating element is outside the exterior wall of the first device;
b. the second device includes a sensor:
(1) in communication with the vibrating element, and
(2) inducing the vibrations therein.

20. An implantable electromedical arrangement including:
a. an implantable heart stimulator having:
(1) an exterior wall, and
(2) a first piezoelectric transducer adjacent the exterior wall;

b. a second piezoelectric transducer adjacent to, and on the opposite side of the exterior wall from, the first piezoelectric transducer;
c. at least one of:
   (1) a heart sensor providing the second piezoelectric transducer with electrical signals representing the status of the heart, and
   (2) a heart actuator providing the heart with heart stimulation pulses, the heart stimulation pulses being delivered in accordance with signals received by the heart actuator from the second piezoelectric transducer.

* * * * *